United States Patent [19]
Heacock

[11] Patent Number: 5,997,141
[45] Date of Patent: Dec. 7, 1999

[54] SYSTEM FOR TREATING THE FUNDUS OF AN EYE

[75] Inventor: Gregory L. Heacock, New York, N.Y.

[73] Assignee: Odyssey Optical Systems, LLC, Boston, Mass.

[21] Appl. No.: 09/036,388

[22] Filed: Mar. 6, 1998

[51] Int. Cl.[6] ..................................................... A61B 3/14
[52] U.S. Cl. .............................................. 351/221; 606/4
[58] Field of Search .................................... 351/205, 206, 351/210, 211, 216, 220, 221; 606/4

[56] References Cited

U.S. PATENT DOCUMENTS

| | | |
|---|---|---|
| 4,768,874 | 9/1988 | Webb et al. . |
| 4,856,891 | 8/1989 | Pflibsen et al. ........................ 351/210 |
| 5,568,208 | 10/1996 | Van De Velde ........................ 351/221 |
| 5,633,695 | 5/1997 | Feke et al. .............................. 351/221 |

*Primary Examiner*—George Manuel
*Attorney, Agent, or Firm*—McAndrews, Held & Malloy, Ltd

[57] ABSTRACT

The system of the present invention allows the interior of the eye to be viewed and simultaneously treated with a laser without the use of an optic in contact with the eye. The system scans illumination light into the eye so that the interior of the eye can be observed and includes an integral treatment laser that can be directed to a desired position in the interior of the eye including the fundus. Light reflected from the patient's eye and received by the system may be observed directly by the physician via an eyepiece lens. In a preferred embodiment, however, the reflected light is applied to an image detector that is coupled to a display for displaying an image of the interior of the patient's eye. Because the physician can view the interior of the eye via the display during treatment, unwanted reflections of the treatment laser to the physician's eye via the viewing system are prevented.

68 Claims, 4 Drawing Sheets

SYSTEM FOR TREATING THE FUNDUS OF AN EYE

CROSS-REFERENCE TO RELATED APPLICATIONS

This application is related to U.S. patent application Ser. No. 08/629,584 filed Apr. 9, 1996 and issued as U.S. Pat. No. 5,784,148; U.S. Pat. No. 5,673,097 and U.S. patent application Ser. No. 08/951,535 now U.S. Pat. No. 5,861,939.

TECHNICAL FIELD

The present invention is directed to a system for treating the interior of the eye including the fundus; and more particularly to a system that scans illumination light into the eye so that the interior can be viewed and having an integral treatment laser that can be directed to any desired position within the illuminated area.

STATEMENT REGARDING FEDERALLY SPONSORED RESEARCH OR DEVELOPMENT

N/A

BACKGROUND OF THE INVENTION

Various types of scanning laser ophthalmoscopes such as shown in U.S. Pat. Nos. Webb 4,765,730; Webb 4,764,006; Webb 4,768,873 and Kobayashi 4,781,453 are known for scanning a laser that is directed onto the fundus of a patient's eye to allow an interior portion of the eye to be viewed on a display for diagnostic purposes alone.

In order to treat the eye after diagnosis, different devices are currently used. For example, methods for treatment typically employ bright, white light provided by a slit lamp or the like which is shone into the patient's eye. While the eye is thus illuminated, the physician holds a prismatic or focusing contact lens so that it touches the cornea of the patient's eye and then directs a treatment laser through the contact lens. There are several disadvantages associated with this method of treatment. Bright, white light shone into a dilated eye is uncomfortable for the patient. Moreover, when procedures are lengthy, such as a panretinal photocoagulation which can take up to an hour, bright, white light exposure to the retina can approach damaging levels. Further, manipulations of the contact lens, as may be necessary during a procedure, can cause corneal abrasions. Contact of the lens with the eye can also result in the transmission of diseases. Since the contact lens is hand held, unintentional movement can also result in misdirection of the treatment laser.

BRIEF SUMMARY OF THE INVENTION

In accordance with the present invention, the disadvantages of prior systems for treating the fundus of an eye have been overcome. The system of the present invention allows the interior of the eye to be illuminated with scanned light and viewed during treatment with a laser without the need of a contact lens or bright, white light.

More particularly, the scanning system scans a two dimensional area of illumination that is directed onto the fundus to illuminate the interior of the eye. The illumination light can be coherent light such as generated by a laser or non-coherent light such as generated by LEDs. Light reflected from the eye is captured so that an image of the interior of the eye can be viewed via a display or an eyepiece lens. While the interior of the eye is being viewed, an aiming beam of a treatment laser is directed to a desired position on the fundus, or other interior portion of the eye, by a steering system. When the desired position of the treatment laser is reached, a treatment beam that is coaxial with the aiming beam is actuated to form a small therapeutic burn or otherwise treat the eye.

The steering system of the present invention includes one or more movable optics to change the focal plane of the treatment light and to change the position of the treatment light within that plane. A size control optic is also provided for varying the size of the spot of the treatment light.

The system of the present invention is a non-contact system for treating various conditions in the eye so that the risk of corneal abrasions and disease transmission via a contact lens or the like is eliminated. Further, because the illumination light is scanned in accordance with the system of the present invention, it can use lower light levels to illuminate the interior of the eye than heretofore possible. Moreover, in the preferred embodiment, where the eye can be observed during treatment via a display, there is no risk of unwanted reflections of the treatment beam reaching the physician's eye. With this embodiment of the invention, the physician can view the interior of the eye when the treatment beam is actuated. In the embodiment that utilizes an eyepiece lens, a shutter or the like is actuated simultaneously with the treatment beam so that the shutter blocks unwanted reflections of the treatment beam from reaching the physician's eye.

These and other advantages and novel features of the present invention, as well as details of an illustrated embodiment thereof, will be more fully understood from the following description and drawings.

DETAILED DESCRIPTION OF THE INVENTION

Figure 1:
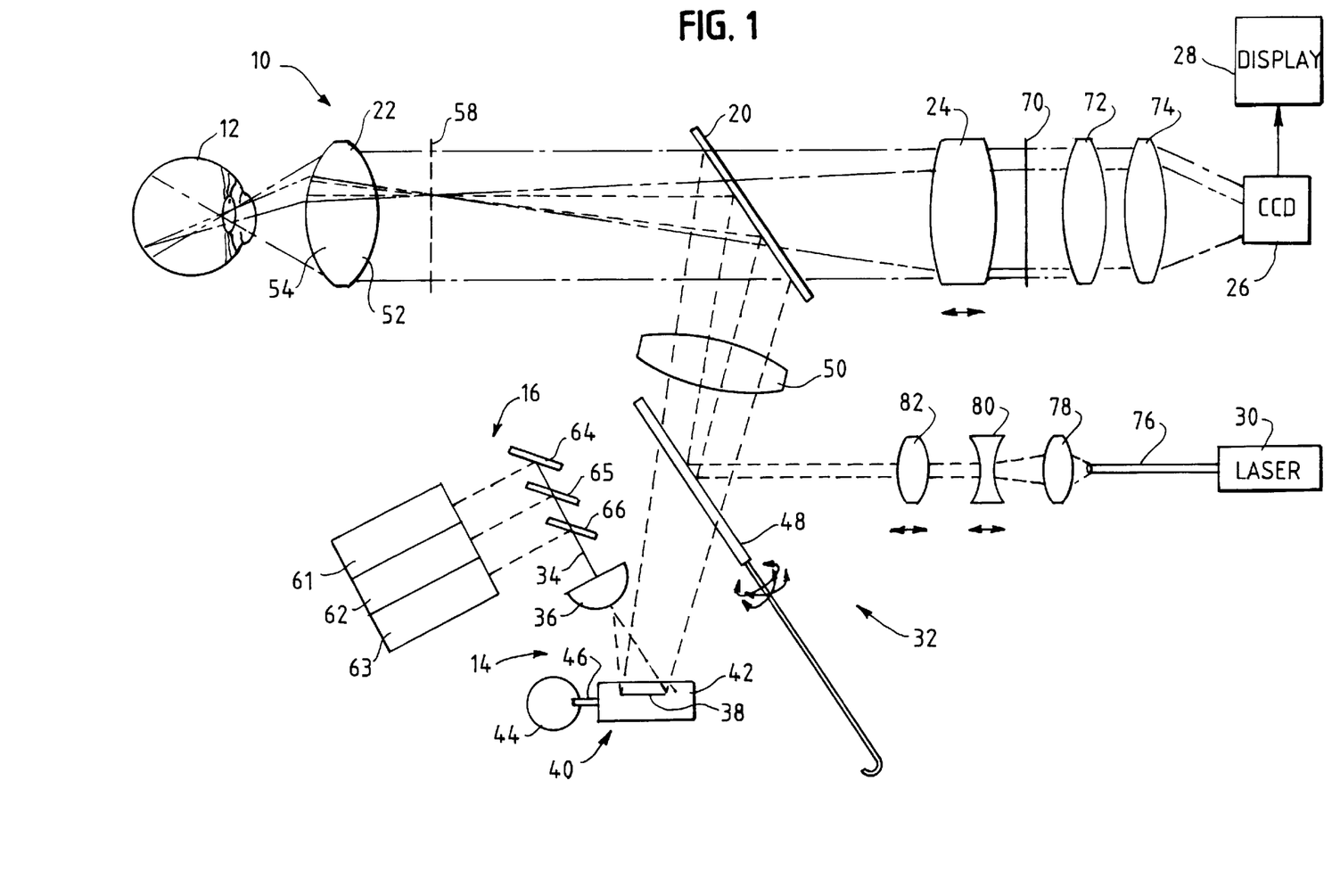
FIG. 1 is a plan view of the system for treating the fundus of an eye in accordance with the present invention.

A system or device 10 for treating the fundus of a patient's eye 12 while illuminating the fundus with scanned light for viewing is illustrated in FIG. 1. The system 10 includes a scanning system 14 that receives light from a source 16 and scans a two dimensional area of illumination that is directed to the fundus of the eye 12 by a beam splitter 20 and a lens 22 so as to illuminate the interior of the eye 12. The illumination light reflected from the patient's eye 12 is received by the lens 22 and passes through the beam splitter 20 to a movable field lens 24. The position of the field lens is varied to focus on images at varying depths within the interior of the eye. The image of the interior of the eye focused on by the lens 24 is captured for detected by a charged coupled device (CCD) camera 26, the output of which is coupled to a display 28 so that a physician can view the detected image. A treatment laser 30 is used to treat various conditions in the interior of the eye without the need of an optic in contact with the patient's eye. A steering system 32, manipulatable by a physician, directs the treatment laser to the desired position within the interior of the eye. The system components may be contained in or mounted on a compact housing, not shown.

The illumination light source 16 generates a beam 34 of light that impinges on a first scanning element 36. The first scanning element 36 is a passive, stationary optical element such as a cylindrical lens that generates a line 38 of light from the point of light impinging on the lens 36. The line 38 of light is then scanned in a direction perpendicular to the length of the line by a second scanning element 40. The second scanning element 40 may include for example a scanner mirror 42 that is driven by a motor 44 coupled to the mirror 42 by a shaft 46. As the scanner mirror 42 vibrates, it scans the line of light 38 across the face of the beam splitter 20 so as to scan a two dimensional area of illumination. As the illumination light is scanned it passes through a specific reflector 48 and a lens 50. The specific reflector 48 is such that it reflects the wavelength of the treatment light from the source 30 and passes all other wavelengths of light. The beam splitter 20 reflects the two dimensional area of illumination as it is scanned towards the eye 12 so that it is centered on the real image plane 58 and the lens 22. The illumination light as it travels towards the eye is slightly diverging. The lens 22 is preferably an aspheric lens with a weaker surface 52 that makes the slightly diverging illumination light parallel and directs the light to the stronger surface 54 of the lens 22. The stronger surface 54 of the aspheric lens 22 focuses the illumination light to a point 88 that is centered on the patient's pupil or generally proximate thereto. The illumination light continues its path until it strikes the retina of the eye 12, thus illuminating an area of the patient's eye.

The scanners 36 and 40 used to scan a two dimensional area of illumination directed to the eye 12 can take forms other than depicted in FIG. 1. For example, acousto optic modulators can be used or various types of scanners with moving mirrors. The use of a passive optical element 36 to scan or convert a point of light to a line of light however simplifies the optical system and allows a color image of the interior of the patient's eye at varying depths within the eye to be obtained very easily.

In particular, the light beam 34 may be formed of a single wavelength of coherent light such as a laser. Alternatively, the source of illumination light 16 may include a number of lasers 61–63, each of which produces a laser beam of a different wavelength preferably associated with blue, green and red laser light. The laser light of different wavelengths generated by the lasers 61–63 are combined to form a single beam 34 by a number of dichroic mirrors 64–65. Each of the dichroic mirrors has a coating so that the mirror reflects only the wavelength of light associated with its respective laser source. In particular, the dichroic mirror 64 reflects light having a wavelength of the source 61. This reflected light passes through the dichroic mirror 65 where it is combined with coaxial light reflected by the mirror 65 from the laser source 62 thus combining light of the two wavelengths associated with the lasers 61 and 62. This combined beam passes through the dichroic mirror 66 where it is combined with light having the selected wavelength of the laser 63 that is reflected coaxially therewith so as to form the single beam 34 comprised of the three lasers of different wavelengths from the sources 61–63.

As the beam 34 is scanned onto the patient's eye 12, different parts of the eye at different depths therein respond to different wavelengths of laser light by reflecting laser light of a particular wavelength. The light reflected from the patient's eye 12 is received and focused by the aspheric lens 22 to a point on the image plane 58. The reflective light then passes through the beam splitter 20 to the movable field lens 24. From the field lens 24, the reflected light passes through a polarizer film 70 to focusing optics comprised of a pair of lenses 72 and 74 of the CCD camera 26. The lenses 72 and 74 focus the rays reflected from the patient's eye onto the image plane of the CCD camera 26.

By changing the position of the field lens 24 so that it is moved farther from the patient's eye, the real image plane 58 shifts to a position that is closer to the beam splitter 20. With this shift in the image plane, the image focused on the CCD camera 118 is an image plane in the interior of the eye 12, closer to the front of the eye. Thus, by merely moving the field lens 24 to a different position, various images of the interior of the patient's eye 12 at varying depths therein can be obtained. Further, by coupling the CCD camera to a color display 28, as the field lens 34 is moved to bring into focus an image at varying depths within the interior of the patient's eye, the image displayed on the color display 28 automatically changes to display the changed image in the color of the associated wavelength of laser light that is reflected by the portion of the eye at that particular depth.

In order to pass only desired light to the detection circuitry of the CCD camera 26, the laser light from the source 16 is polarized in a first direction and the polarizer film 70 is polarized in a second direction that is different from the first direction. In particular, the polarizer film 70 is preferably polarized in a direction perpendicular to the polarization of the light from the source 16. This polarization of the polarizer film 70 blocks unwanted reflections from the patient's cornea, the aspheric lens 22 and other elements of the system from reaching the image plane of the CCD camera 26 so that only the randomized reflected image from the interior of the patient's eye passes through the optical system to the camera 26.

Further, by orienting the scanning of lines onto the patient's eye in a particular manner with respect to the orientation of a raster line of the CCD camera, beating and blanking problems in the video image depicted on the display 28 from the CCD camera are eliminated. More particularly, the raster lines extend horizontally across the CCD camera 118. The illumination light line 38 when reflected by the beam splitter 20 onto the eye extends in a generally vertical direction and is scanned horizontally. When the line of light is thus scanned on the patient's eye 12 it extends vertically, i.e. perpendicularly, to the direction of the horizontal raster line of the CCD camera. Because the line of light scanned onto the patient's eye 12 extends perpendicular to the direction of the raster line of the CCD camera, beating and blanking problems in the displayed video image are eliminated.

In order to treat various conditions of the interior of the eye 12 as viewed on the display 28, the treatment laser 30 is used. Light from the treatment laser 30 diverges at the exit angle of a fiber optic 76 that directs the light towards a focusing lens 78. The focusing lens 78 directs the light from the treatment laser source 30 to a negative lens 80. The lens 80 is movable to change the size of the spot of the treatment light to a desired size for treating the particular condition in the interior of the eye 12. From the negative lens 80, the light passes through a focusing lens 82 that focuses the light from the treatment laser source 30 at a real image plane outside of the eye and a focal plane in the interior of the eye. The lens 82 is movable so as to change the focal plane of the treatment laser within the interior of the eye 12. The treatment light passing through the movable focusing lens 82 impinges on the specific reflector 48. The specific reflector 48 as discussed above reflects the wavelength of light from the treatment laser source 30 and passes the illumination light from the source 16 therethrough. The reflector 48 is movable so as to direct the treatment light to any point within a given area of the focal plane of the treatment light as discussed below with reference to FIG. 4. The lens 50 is a collimating lens that renders the illumination light from the source 16 parallel and concentrates the illumination light at the image plane 58 so that it is brighter for a given low power level as described below. The collimating lens 50 also operates in conjunction with the lens 82 to focus the treatment light to a point.

In accordance with the present invention, the interior of the patient's eye 12 can be viewed via the display so that the physician can observe the interior of the eye not only for diagnostic purposes but in order to treat various conditions observed in the interior of the eye. In practice, the source of treatment light 30 preferably includes both an aiming beam and a treatment beam. An Argonne laser of this type is available from Coherent Medical, Inc. and a Diode laser of this type is available from Iris Medical, Inc. The physician directs the aiming beam from the source 30 by moving the various optics of the steering system 32 so as to position the aiming beam at a desired location in the interior of the eye 12 for treating the eye. Once the aiming beam is positioned to the desired location as viewed by the physician on the display 28, the physician actuates the treatment beam from the treatment laser source 30 that is coaxial with the aiming beam so as to treat the eye at the position determined by the aiming beam. Because the physician views the interior of the eye 12 during treatment and in particular during the actuation of the treatment beam from the source 30 via the display 28, no unwanted reflections of the treatment laser can reach the physician's eye via the viewing system.

Figure 2:
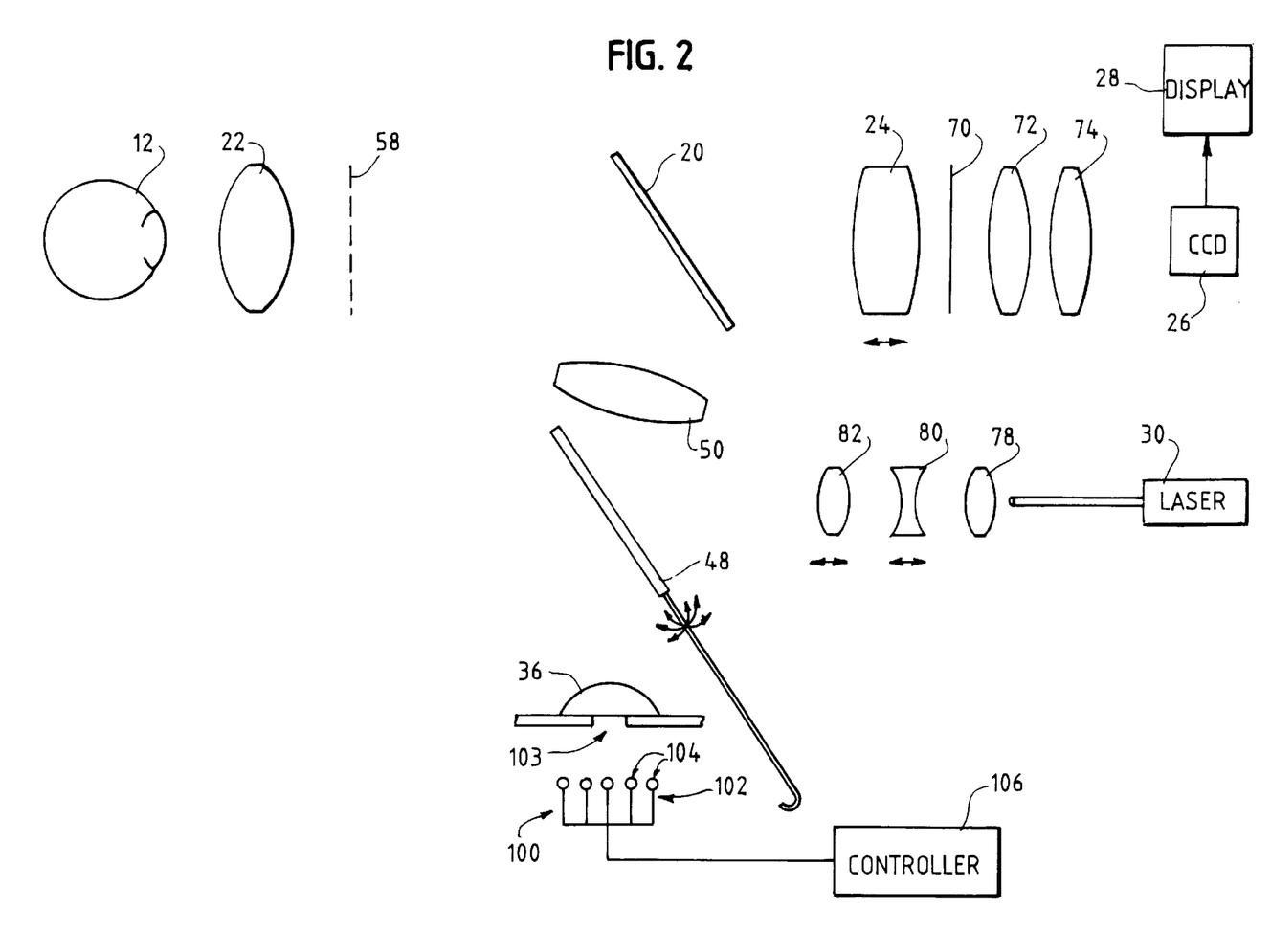
FIG. 2 is a plan view of an alternative embodiment of the system of the present invention with a noncoherent light source for illuminating the eye.

In accordance with another embodiment of the present invention as shown in FIG. 2, light from a noncoherent light source 100 is scanned by a scanning system to illuminate the interior of the patient's eye 12 so that it can be viewed during treatment with the treatment laser 30. The noncoherent light source 100 may include, for example, a linear array 102 of light emitting diodes (LEDs) 104 that can be individually actuated in a sequence. The scanning system in this embodiment includes the cylindrical lens 36 for scanning or converting a point of light from one of the LEDs 104 to a line of light that is reflected by the beam splitter 20 to the lens 22. The light from each of the LEDs 104 passes through a slit aperture 103 to the cylindrical lens 36 wherein the width of the slit 103 is parallel to a diameter of the lens 36. The line of light generated by the cylindrical lens 36 from a single point of light from the array 102 is such that when it is projected onto the beam splitter 20, the line of light extends in a direction that is perpendicular to the line of light which would be projected on the beam splitter 20 if the lens 36 were removed and all of the LEDs in the array 102 were turned on simultaneously. Lines of light are scanned across the beam splitter 20 by the sequential actuation of the LEDs 104 in the array 102 by the controller 106 so as to scan a two dimensional area of illumination directed to the interior of the eye 12. In this embodiment, the collimating lens 50 concentrates light from the LEDs at the image plane so that the power of the illumination light source 100 may be lowered. The illumination light reflected by the patient's eye 12 is received by the aspheric lens 22 and passes through the optics 20, 24, 70, 72 and 74 to the CCD camera 26 so that an image of the interior of the eye 12 can be viewed on the display 28 as discussed above.

It is noted that any type of controller 106 may be used to sequentially actuate the point sources of light in the array 102. The controller 106 may be as simple as a timer coupled to a counter that actuates a switching array coupled to the LEDs 104. Alternatively, a more sophisticated controller such as a microprocessor or the like may be used. The rate of the scan of illumination light generated by the controller 72, the array 102 and cylindrical lens 36 with the slit aperture 103 is preferably between 70 hertz and 90 hertz.

Figure 3:
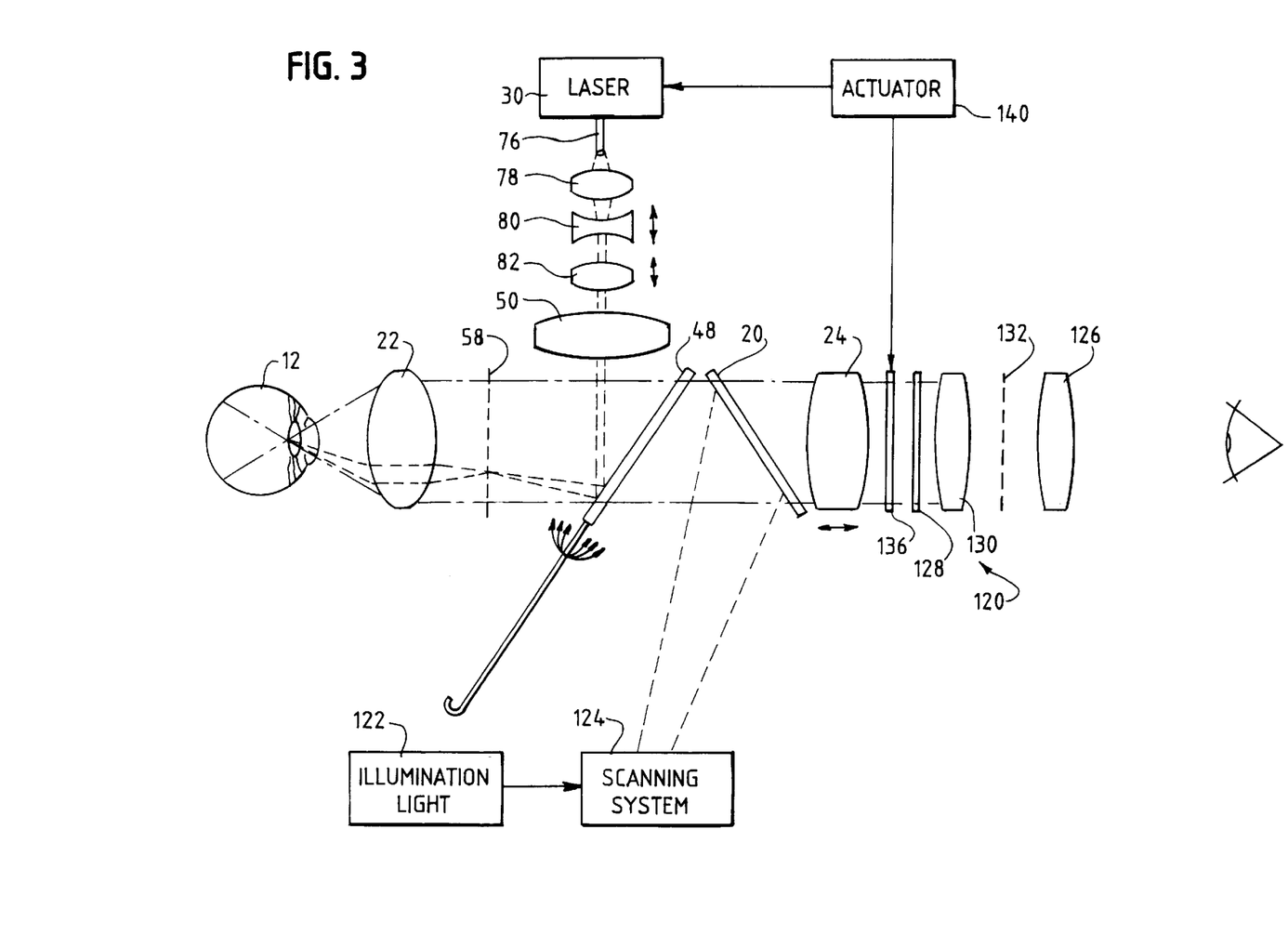
FIG. 3 is a plan view of another embodiment of the system of the present invention having an eyepiece lens.

In a further embodiment of the present invention illustrated in FIG. 3, light reflected from the patient's eye from an illumination light source 122 and scanning system 124 is captured by an optical system 120 so that a magnified image of an interior portion of the patient's eye can be viewed directly by the physician through an eyepiece lens 126. As in previous embodiments, the light reflected from the patient's eye 14 passes through the beam splitter 20 to the field lens 24. The field lens 24 is movable so as to change the position of the image plane 58 closer to or farther from the lens 22. The light reflected from the patient's eye passes through the field lens 24 and from there through a polarizer film 128 to an image lens 130. The image lens 130 and field lens 24 form a magnified image at an image plane 132 of the interior of the patient's eye which is observed by the physician as he looks through the eyepiece lens 126.

In order to pass only desired light to the eyepiece lens 22, the light from the source 122 is polarized in a first direction and the polarizer film 128 of the optical system 120 is polarized in a second direction that is different from the first direction. In particular, the polarizer film 128 is preferably polarized in a direction perpendicular to the polarization of the light from the source 122. This polarization of the polarizer film 112 blocks unwanted reflections from the patient's eye, the aspheric lens 22 and other elements of the system from reaching the image lens 130 and eyepiece lens 126 so that only the randomized reflected image from the interior of the patient's eye passes through the optical system into the eyepiece lens 22.

In order to insure that no treatment laser light passes through the system to the eyepiece lens 126 and to the physician's eye, a shutter 136 is employed. The shutter may be any well-known type of shutter for blocking unwanted treatment laser reflections. It may be for example a glass with a laser safety coating that is moved into position by a solenoid that is actuated by an actuator 140 simultaneously with the actuation of the treatment beam from the treatment laser source 30. Thus, after the physician has steered the aiming beam of the treatment laser to a desired position, the physician actuates a switch forming a portion of the actuator 140. Actuation of the switch 140 simultaneously actuates the shutter 136 and treatment beam so that the shutter is moved into position when the treatment beam is actuated to treat the eye. Unlike the embodiment of FIG. 3 wherein the shutter 136 temporarily blocks the view of the physician during the exact moment when the treatment laser is being applied to the eye 12 so as to protect the physician's eye, the physician's view of the eye 12 is not blocked during the application of the treatment laser to the eye 12 by the embodiments of the invention depicted in FIGS. 1 and 2 wherein the physician views the eye via the display 28.

The embodiment of FIG. 3 also illustrates an alternative position for the treatment laser and steering system 32 wherein the specific reflector 48 is positioned between the beam splitter 20 and the aspheric optic 22. In this embodiment, the light reflected from the patient's eye 12 to the optical system 120 capturing the image to be viewed, passes through the specific reflector 48.

It is noted that the beam splitter 20 separates the scanning system in the various embodiments from the optical path between the patient's eye and the image capturing system which may include the CCD camera 26 and display 28 or the eyepiece lens 126. The beam splitter 20 is a partially reflecting illumination mirror that reflects at least 25% of the illumination light from the scanning system 24 to the patient's eye 14 and that reflects the treatment laser from the source 30 to the patient's eye while passing therethrough light reflected from the patient's eye 14 so that the interior of the eye can be viewed for treatment. The present invention eliminates problems with shading off which can occur when optical elements such as a scanner are placed in the optical path from the patient's eye to the eye image capturing system. These optical elements can block the chief ray from any given image position on its route from the patient's eye to the image capturing optics thereby causing shading off. This problem is eliminated in the present invention by the separation of the image capturing system from the scanning system and by employing optical elements within the optical path from the patient's eye to the eye image capturing system that do not block the chief rays from any given image position on their route to the eye image capturing system.

It should be appreciated, that various combinations of lenses can be used in place of the aspheric lens 22. However, the use of an aspheric lens is desirable because it accomplishes a number of functions with one optical element. The aspheric lens may be such that the surfaces 52 and 54 of the lens are described by the polynomial function:

$$f(Y, A_2, A_4, A_6, C, cc) = $$
$$A_2Y^2 + A_4Y^4 + A_6Y^6 + CY^2 / \left(1 + \sqrt{1 - C^2ccY^2}\right)$$

where $A_2$, $A_4$ and $A_6$ are constants; C represents the curvature of the surface; and cc represents the conic constant. For the stronger surface 54 of the lens 22, these values should be within the following ranges:

$0.0 < A_2 < 0.003$
$-0.02 < A_4 < 0.02$
$-0.01 < A_6 < 0.01$
$-0.1 < C < 0.0$
$-2.0 < cc < 1.0$

For the weaker surface 52 of the lens 22 these values should be within the following ranges:

$-0.003 < A_2 < 0.0$
$0.0 < A_4 < 0.001$
$-0.001 A_6 < 0.001$
$0.03 < C < 0.06$
$-2.0 < cc < 0.0$

Further the curvature C of the weaker surface 52 is preferably greater than $-1/2$ times the curvature C of the stronger surface 54.

In a preferred embodiment of the present invention, the stronger surface 62 of the lens 60 has the values of: $A_2=0.000444$, $A_4=0.000001$, $A_6=0.0$, $C=-0.092$ and $cc=-0.933$; whereas the weaker surface 52 of the lens 22 has values of: $A_2=-0.00243$, $A_4=0.0000012$, $A_6=0.0$, $C=0.045$ and $cc=-1.213$.

While the diameter d of the lens 22 may be varied, the preferred diameter is 35 millimeters. The aspheric lens 22 produces a 60° field of view for the system 10. Further, the real image produced by the aspheric lens 22 is substantially free from distortions.

Figure 4:
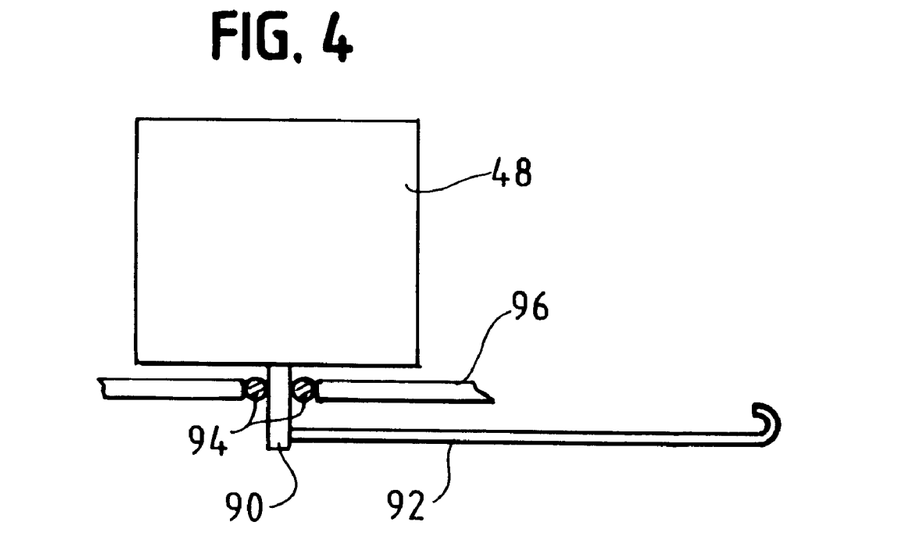
FIG. 4 is a partial cross-sectional view of a movable optic for varying the position of the treatment light within the focal plane thereof.

An example of a suitable mounting for the specific reflector 48 that allows the reflector 48 to be rotated or pivoted in a plurality of directions is depicted in FIG. 4. The mirror 48 is attached to a shaft 90 that extends through an O-ring 94 that is supported in an aperture of a housing 96 for the mirror 48. The shaft 90 is attached to a rod 92 that is engageable by a doctor to move the position of the mirror 48. This arrangement allows the mirror 48 to be pivoted in a large number of directions about a point generally at the center of the O-ring 94. The physician, by manipulating the rod 92 can thus vary the position of the mirror 48 so as to direct the aiming beam of the treatment laser 30 to a desired location in the focal plane of the treatment laser as determined by the position of the lens 82. A desired point in the interior of the eye 12 can thus be treated with the treatment beam of the treatment laser from the source 30.

Figure 5:
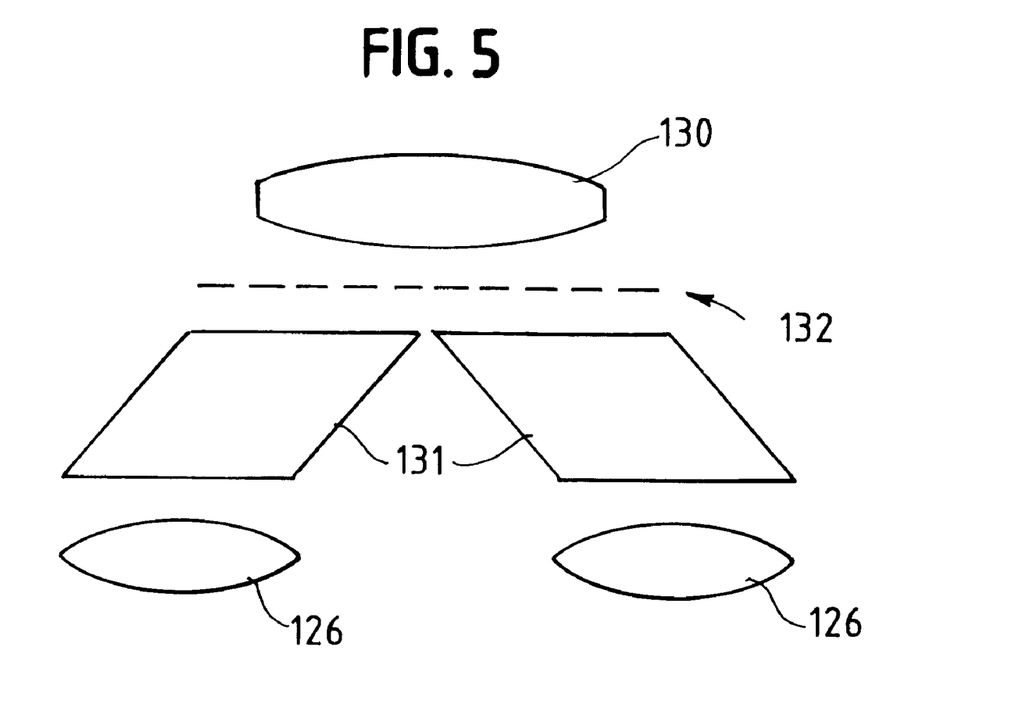
FIG. 5 is a top view of a binocular eyepiece viewing arrangement.

The eyepiece lens viewing system depicted in FIG. 3 may be monocular having a single eyepiece lens 126 or it may be binocular having an optic(s) to direct the image to the physician's right eye and left eye through a pair of eyepiece lenses. A suitable binocular eyepiece lens viewing system is depicted in FIG. 5. The magnified image at the image plane 132 from the image lens 130 is directed by a rhomboid prism pair 131 to a respective eyepiece lens 126 and 126' for the physician's right eye and left eye.

The treatment system of the present invention does not require contact with the eye 12 as is required with prior systems. Thus, the risk of corneal abrasion and disease transmission via contact with the eye is eliminated. Moreover, because the illumination light is scanned, the need for bright, white light illumination is eliminated and the illumination system in accordance with the present invention is much more comfortable for the patient. The treatment laser and associated steering system allows the physician to treat conditions within the eye 12 that occur at various locations therein. Further, the use of an image capturing system that employs a display depicting an image of the interior of the eye 12 allows the physician to view the eye during the instant of treatment since unwanted reflections from the treatment laser cannot reach the physician via the display.

It should be apparent that many modifications to the system of the present invention can be made by combining the optical elements thereof, repositioning the optical elements and/or substituting multiple optical elements for one particular element. Thus, it is to be understood that within the scope of the appended claims, the invention may be practiced otherwise than as described hereinabove.

I claim:

1. A system for viewing and treating the interior of the eye including the fundus comprising:
    a source of illumination light;
    a scanning system for scanning a two dimensional area of illumination with said illumination light;
    a source of laser light for treatment;
    an optical system for directing the scanned illumination light onto the fundus of the eye and for receiving light reflected from the patient's eye for observation; and
    a steering system for directing the treatment light to various positions in the illuminated interior of the eye.

2. A system for viewing and treating the interior of the eye as recited in claim 1 wherein the source of illumination light generates coherent light.

3. A system for viewing and treating the interior of the eye as recited in claim 1 wherein the source of illumination light generates noncoherent light.

4. A system for viewing and treating the interior of the eye as recited in claim 1 including a device responsive to the light reflected from the patient's eye to detect an image of the interior of the eye and a display for displaying the detected image so that the image can be viewed during treatment.

5. A system for viewing and treating the interior of the eye as recited in claim 1 further including at least one eyepiece lens for receiving reflected light from the optical system and through which a clinician looks to directly view an image of the illuminated area of the patient's eye.

6. A system for viewing and treating the interior of the eye as recited in claim 5 including a shutter operable to block reflections from said treatment laser to said eyepiece lens.

7. A system for viewing and treating the interior of the eye as recited in claim 1 wherein said steering system includes an optic movable to change the position of the treatment light within a focal plane of the laser.

8. A system for viewing and treating the fundus of the eye as recited in claim 1 wherein said steering system includes an optic movable to change the position of a focal plane of the treatment light.

9. A system for viewing and treating the fundus of the eye as recited in claim 1 including an optic movable to change the size of a spot of the treatment light.

10. A system for viewing and treating the fundus of the eye as recited in claim 1 wherein said optical system includes image capturing optics to allow observation of a plane in the interior of the eye, said image capturing optics including a movable lens for varying the plane of the eye observed.

11. A system for viewing and treating the interior of the eye including the fundus comprising:
    a source of illumination light;
    a scanning system for scanning a two dimensional area of illumination with said illumination light;
    a source of laser light for treatment;
    an optical system for directing the scanned illumination light onto the fundus of the eye and for receiving light reflected from the patient's eye;
    a first optic for receiving from said optical system light reflected from the patient's eye, the first optic being movable so as to bring into focus different parts of the user's eye at various depths therein for observation;
    a second optic movable to change a focal plane of the treatment light for focusing the treatment light at various depths within the eye; and
    a third optic movable to vary the position of the treatment light within the focal plane of the treatment light.

12. A system for viewing and treating the interior of the eye as recited in claim 11 wherein said third optic is a movable reflector that reflects the treatment light and passes there through illumination light.

13. A system for viewing and treating the interior of the eye as recited in claim 11 including a beam splitter disposed in the path of the illumination light between the scanning system and the eye and disposed in the path of the reflected light between the eye and the first optic to separate a portion of the paths.

14. A system for viewing and treating the interior of the eye as recited in claim 13 wherein said third optic is disposed between the scanning system and the beam splitter.

15. A system for viewing and treating the interior of the eye as recited in claim 13 wherein said third optic is disposed between the beam splitter and the user's eye.

16. A system for viewing and treating the interior of the eye as recited in claim 11 including an optic movable to change the size of a spot of the treatment light.

17. A system for viewing and treating the interior of the eye as recited in claim 11 wherein the source of illumination light generates coherent light.

18. A system for viewing and treating the interior of the eye as recited in claim 11 wherein the source of illumination light generates noncoherent light.

19. A system for viewing and treating the interior of the eye as recited in claim 11 including a device responsive to the light reflected from the patient's eye to detect an image of the interior of the eye and a display for displaying the detected image so that the image can be viewed during treatment.

20. A system for viewing and treating the interior of the eye as recited in claim 11 wherein the optical system includes an eyepiece lens through which a clinician looks to directly view an image of the illuminated area of the patient's eye.

21. A system for viewing and treating the interior of the eye as recited in claim 21 including a shutter operable to block reflections from said treatment laser to said eyepiece lens.

22. A system for viewing and treating the interior of the eye including the fundus comprising:
    a source of illumination light;
    a scanning system for scanning a two dimensional area of illumination with said illumination light;
    a source of laser light for treatment;
    an optical system for directing the scanned illumination light onto the fundus of the eye and for receiving light reflected from the patient's eye;
    a field lens receiving, from said optical system, light reflected from the patient's eye, said field lens being movable so as to bring into focus different parts of the user's eye at various depths therein; and
    a treatment light positioning optic disposed in the path between the source of treatment light and the eye and movable to vary the position of the treatment light within the eye's interior.

23. A system for viewing and treating the interior of the eye as recited in claim 22 wherein said treatment light positioning optic is a movable reflector that reflects the treatment light and passes therethrough illumination light.

24. A system for viewing and treating the interior of the eye as recited in claim 22 including a movable optic to vary a focal plane of the treatment light.

25. A system for viewing and treating the interior of the eye as recited in claim 22 including a size control optic disposed in the path between the source of treatment light and the eye and moveable to change the size of a spot of the treatment light on the fundus.

26. A system for viewing and treating the interior of the eye as recited in claim 22 wherein the source of illumination light generates coherent light.

27. A system for viewing and treating the interior of the eye as recited in claim 22 wherein the source of illumination light generates noncoherent light.

28. A system for viewing and treating the interior of the eye as recited in claim 22 including a device responsive to the light reflected from the patient's eye to detect an image of the interior of the eye and a display for displaying the detected image so that the image can be viewed during treatment.

29. A system for viewing and treating the interior of the eye as recited in claim 22 wherein the optical system includes an eyepiece lens through which a clinician looks to directly view an image of the illuminated area of the patient's eye.

30. A system for viewing and treating the fundus of the eye as recited in claim 29 including a shutter operable to block reflections from said treatment laser to said eyepiece lens.

31. A system for viewing and treating the interior of the eye as recited in claim 22 wherein said treatment light includes an aiming light beam and a treatment light beam wherein the aiming light beam is useable to locate the position at which the treatment light beam is to be actuated.

32. A system for viewing and treating the interior of the eye including the fundus comprising:
    a source of illumination light;
    a scanning system for scanning a two dimensional area of illumination with said illumination light;
    a source of laser light for treatment;
    an optical system for directing the scanned illumination light onto the fundus of the eye and for receiving light reflected from the patient's eye; and
    a treatment light positioning optic disposed in the path between the source of treatment light and the eye and movable to vary the position of the treatment light within the interior of the eye.

33. A system for viewing and treating the interior of the eye as recited in claim 32 wherein said treatment light positioning optic is movable to vary the position of a focal plane of the treatment light.

34. A system for viewing and treating the interior of the eye as recited in claim 32 wherein said treatment light positioning optic is movable to vary the position of the treatment light within a focal plane of the treatment light.

35. A system for viewing and treating the interior of the eye as recited in claim 32 including an optic movable to change the size of a spot of the treatment light.

36. A system for viewing and treating the interior of the eye including the fundus comprising:
    a source of illumination light;
    a scanning system for scanning a two dimensional area of illumination with said illumination light;
    a source of laser light for treatment;
    an optical system for directing the scanned illumination light onto the fundus of the eye and for receiving light reflected from the patient's eye;
    at least one movable positioning optic for directing the treatment light to various positions in the interior of the eye; and
    a size control optic for varying the size of a spot of the treatment light on the fundus.

37. A system for viewing and treating the interior of the eye as recited in claim 36 wherein said positioning optic is movable to change the focal plane of the treatment light.

38. A system for viewing and treating the interior of the eye as recited in claim 36 wherein said positioning optic is movable to change the position of the treatment light within a given plane.

39. A system for viewing and treating the interior of the eye as recited in claim 36 wherein the source of illumination light generates coherent light.

40. A system for viewing and treating the interior of the eye as recited in claim 36 wherein the source of illumination light generates noncoherent light.

41. A system for viewing and treating the interior of the eye as recited in claim 36 including a device responsive to the light reflected from the patient's eye to detect an image of the interior of the eye and a display for displaying the detected image so that the image can be viewed during treatment.

42. A system for viewing and treating the interior of the eye as recited in claim 36 further including at least one eyepiece lens for receiving reflected light from the optical system and through which a clinician looks to directly view an image of the illuminated area of the patient's eye.

43. A system for viewing and treating the fundus of the eye comprising:
    a source of illumination light;
    a scanning system for scanning a two dimensional area of illumination with said illumination light;
    a source of laser light for treatment;
    an optical system for directing the scanned illumination light onto the fundus of the eye and for receiving light reflected from the patient's eye; and
    a treatment light directing system disposed in the path between the source of treatment light and the eye and including at least one movable optic to vary the position of the treatment light in the interior of the eye.

44. A system for viewing and treating the interior of the eye including the fundus comprising:
    a scanning system for scanning a two dimensional area of illumination directed to the patient's eye to illuminate the interior thereof;
    a treatment laser system for directing a treatment laser to a desired position within the interior of the eye; and
    an image capturing system for receiving light reflected from the patient's eye and detecting an image therefrom, said image capturing system including a display for displaying the detected image for observation during treatment.

45. A system for viewing and treating the interior of the eye as recited in claim 44 wherein said scanning system includes a source of coherent light.

46. A system for viewing and treating the interior of the eye as recited in claim 44 wherein said scanning system includes a source of noncoherent light.

47. A system for viewing and treating the interior of the eye as recited in claim 44 wherein said treatment laser includes an aiming beam and a treatment beam.

48. A system for viewing and treating the interior of the eye as recited in claim 44 wherein said treatment laser system includes at least one optic movable by the physician to vary the position of the treatment laser.

49. A system for viewing and treating the interior of the eye as recited in claim 44 wherein said treatment laser system includes at least one optic movable to vary the size of a spot of the treatment laser.

50. A system for viewing and treating the interior of the eye as recited in claim 44 wherein said image capturing system includes a movable optic for obtaining images at varying depths within the eye.

51. A system for viewing and treating the interior of the eye as recited in claim 44 including a beam splitter disposed in the path between scanning system and the eye and in the path between the image capturing system and the eye to separate a portion of said paths.

52. A system for viewing and treating the interior of the eye as recited in claim 44 wherein said treatment laser system includes a specific reflector for reflecting the treatment laser and passing the illumination light, said specific reflector being positioned in the path of the illumination light from the scanning system to the eye.

53. A system for viewing and treating the interior of the eye as recited in claim 52 wherein said specific reflector is positioned in the path of light reflected from the eye to the image capturing system.

54. A system for viewing and treating the interior of the eye as recited in claim 52 wherein said specific reflector is movable to vary the position of the treatment laser.

55. A system for viewing and treating the interior of the eye including the fundus comprising:

- a scanning system for scanning a two dimensional area of illumination directed to the patient's eye to illuminate the interior thereof;
- a treatment laser system for directing a treatment laser to a desired position within the interior of the eye; and
- an image capturing system for receiving light reflected from the patient's eye and including at least one eyepiece lens through which a clinician looks to view an image of an illuminated area of the interior of the patient's eye.

56. A system for viewing and treating the interior of the eye as recited in claim 55 including a shutter operable to block reflections from the treatment laser to the eyepiece lens.

57. A system for viewing and treating the interior of the eye as recited in claim 55 wherein said scanning system includes a source of coherent light.

58. A system for viewing and treating the interior of the eye as recited in claim 55 wherein said scanning system includes a source of noncoherent light.

59. A system for viewing and treating the interior of the eye as recited in claim 55 wherein said treatment laser includes an aiming beam and a treatment beam.

60. A system for viewing and treating the interior of the eye as recited in claim 55 wherein said treatment laser system includes at least one optic movable by the physician to vary the position of the treatment laser.

61. A system for viewing and treating the interior of the eye as recited in claim 55 wherein said treatment laser system includes at least one optic movable to vary the size of a spot of the treatment laser.

62. A system for viewing and treating the interior of the eye as recited in claim 55 wherein said image capturing system includes a movable optic for obtaining images at varying depths within the eye.

63. A system for viewing and treating the interior of the eye as recited in claim 55 including a pair of eyepiece lenses and an image directing optical system for directing light reflected from the patient's eye to each of said eyepiece lenses.

64. A system for viewing and treating the interior of the eye as recited in claim 63 wherein said optical system includes a rhomboid prism pair.

65. A system for viewing and treating the interior of the eye as recited in claim 55 including a beam splitter disposed in the path between scanning system and the eye and in the path between the image capturing system and the eye to separate a portion of said paths.

66. A system for viewing and treating the interior of the eye as recited in claim 65 wherein said specific reflector is positioned in the path of light reflected from the eye to the image capturing system.

67. A system for viewing and treating the interior of the eye as recited in claim 65 wherein said specific reflector is movable to vary the position of the treatment laser.

68. A system for viewing and treating the interior of the eye as recited in claim 55 wherein said treatment laser system includes a specific reflector for reflecting the treatment laser and passing the illumination light, said specific reflector being positioned in the path of the illumination light from the scanning system to the eye.

* * * * *